United States Patent [19]
Adkins et al.

[11] Patent Number: 5,143,065
[45] Date of Patent: Sep. 1, 1992

[54] IMPLANTABLE DEVICE WITH CIRCADIAN RHYTHM ADJUSTMENT

[75] Inventors: Robert A. Adkins, Angleton; Ross G. Baker, Jr., Houston, both of Tex.

[73] Assignee: Intermedics, Inc., Angleton, Tex.

[21] Appl. No.: 463,233

[22] Filed: Jan. 10, 1990

Related U.S. Application Data

[62] Division of Ser. No. 336,093, Apr. 11, 1989, Pat. No. 4,922,930.

[51] Int. Cl.[5] ............................................. A61N 1/362
[52] U.S. Cl. ............................................. 128/419 PG
[58] Field of Search ............ 128/419 PG, 420.6, 738; 604/65, 66, 67

[56] References Cited

U.S. PATENT DOCUMENTS 4,003,379  1/1977  Ellinwood, Jr. .................. 604/891.1
4,390,022  6/1983  Calfee ........................... 128/419 PG
4,722,342  2/1988  Amundson ....................... 128/419 PG
4,922,930  5/1990  Adkins ........................... 128/419 PG

FOREIGN PATENT DOCUMENTS

WO86072  11/1970  PCT Int'l Appl. .

Primary Examiner—William E. Kamm
Assistant Examiner—Scott M. Getzow
Attorney, Agent, or Firm—John R. Merkling

[57] ABSTRACT

A body function assistance device, capable of analyzing changing but cyclic physiologic needs of a patient and generating a response based on the analysis. A microprocessor in the body function assistance device controls the response of the device to various external events and internal timer events. The microprocessor recognizes variations in patterns of recurrent events and adjusts the output of the body function assistasnce device in response to the detected variations. In a particular embodiment, an implantable cardiac pacer is responsive to a circadian wake-sleep cycle.

33 Claims, 10 Drawing Sheets

IMPLANTABLE DEVICE WITH CIRCADIAN RHYTHM ADJUSTMENT

This is a divisional of copending application(s) Ser. No. 07/336,093 filed on Apr. 11, 1989, now U.S. Pat. No. 4,922,930.

FIELD OF THE INVENTION

This invention relates to implantable body function assistance devices and, more particularly, to implantable devices having variable output parameters and utilizing microprocessor circuitry for sensing changing physiologic needs and controlling the output parameters.

BACKGROUND OF THE INVENTION

A variety of devices exist which may be implanted in a patient's body to supplement or replace natural body functions. Typically, devices may be used to assist the heart in maintaining the steady pumping action needed to sustain life, to control bladder functions, to assist in countering pain-producing nerve impulses, and to control the infusion of various solutions into the body. Such devices may be implanted in the patient for long periods of time, during which the patient may encounter a variety of situations placing different demands on the patient's body. These demands may be transient and substantially random or they may be recurring, and display a circadian or other cycle. Preferably, an implantable body function assistant device should, therefore, be capable of adapting to changing physiologic needs.

In the developing generation of body function assistance devices, digital electronics are replacing analog electronics, which were originally used in such devices. Using digital techniques, body function assistance devices may be made which are more versatile than analog devices. Digital counters and storage registers, combined with improved techniques for communicating information between an external device and an implanted device, make it possible to vary the output parameters of a digital device to suit a variety of physiologic conditions. Even digital devices, however, have generally not analyzed changing physiologic needs and generated a response which is interactive with the analysis, without external intervention.

The electronics art has now developed microprocessors, devices which incorporate the electronic components necessary to perform arithmetic calculations and logic functions with the small size needed for implantable devices. A microprocessor has the capability of accepting data from various sensors, analyzing the data, and generating a response appropriate for the particular analysis without external intervention. Such devices, however, have a relatively high power consumption level. Moreover, if the operating routine of an implanted body function device is actually changed, random access memory (RAM) is typically required. Use of RAM requires considerably more energy than does read only memory (ROM), where the instructions are fixed in the memory. A microprocessor-based body function assistance device capable of responding to changing physiologic needs would, therefore, require an optimized program structure to minimize power consumption while responding to both transient and cyclic physiologic needs. Excessive power consumption could substantially reduce the useful life of an implanted device, which has, typically, a lithium battery power supply, which is a finite source of energy.

These, and other problems, have been solved by Applicants herein for an implantable body function assistance device.

SUMMARY OF THE INVENTION

The Applicants have invented an improved body function assistance device, capable of analyzing changing but cyclic physiologic needs of a patient and generating a response based on the analysis. A microprocessor in the body function assistance device controls the response of the device to various external events and internal timer events. The microprocessor recognizes variations in patterns of recurrent events and adjusts the output of the body function assistance device in response to the detected variations during a, circadian or twenty-four hour, cycle, such as the cycle associated with wake-sleep periods. During a cycle, the microprocessor generates an immediate output to meet present physiologic demands based on a predicted pattern of expected physiologic needs, monitors sensors for indications of variations from a predicted pattern of events, and modifies the predicted pattern of expected future physiologic needs. The improved body function assistance device, therefore, is responsive both to cyclic physiologic needs and to changes in cyclic patterns of physiologic needs.

In a preferred embodiment, disclosed herein, an implantable cardiac pacer is provided wherein the microprocessor is responsive to a circadian wake-sleep cycle. The predicted cycle of physiologic needs models a typical pattern of waking and sleeping periods for the patient. An internal real time clock is provided. At selected intervals during a period of time, the microprocessor implements operating routines to increase or decrease the output of the cardiac pacer pursuant to a logical model of the cyclic physiologic needs of the patient. The microprocessor also periodically samples the output of sensors. On the basis of the sampled output, the microprocessor projects new times for changes in physiologic needs. The microprocessor then modifies the predicted model of circadian physiologic needs, based both on the former selected times and the new projected times, as related by a damping function. The damping function inhibits oscillation of the model and filters detected phenomenon not related to the wake-sleep cycle. A time related to the beginning of a sleep period and a time related to the beginning of a wake period are constrained within maximum and minimum time limits, so that an unduly long or short sleep period will be avoided.

With the foregoing in mind, it is a principle object of the present invention to provide an implantable body function assistance device responsive to cyclic variations in physiologic needs.

Another important object of the present invention is to provide a body function assistance device wherein a predicted cyclic output is modified in response to sensed events.

A further important object of the present invention is to provide a microprocessor driven implantable body function assistance device capable both of responding to immediate physiologic requirements and of predicting and responding to future cyclic physiologic requirements.

It is also an object of the present invention to provide an implantable body function assistance device wherein the modification of predicted cyclic output correlates former selected values with new projected values.

Another object of the present invention is to provide a device which inhibits oscillation of a predictive model of cyclic output in an implantable body function assistance device.

It is also an object of the present invention to provide an implantable body function assistance device responsive to cyclic physiologic requirements which filters detected phenomenon not related to the selected cycle.

These and other objects and features of the present invention will be apparent from the detailed description taken with reference to the accompanying drawings.

DETAILED DESCRIPTION OF A PREFERRED EMBODIMENT

Reference is now made to the drawings, wherein a preferred embodiment of an implantable body function assistance device is disclosed and wherein like numerals designate like parts or processes throughout. The various methods and apparatus described herein may be employed in a variety of implantable devices, incorporating a microprocessor or state machine and periodically responsive to cyclic and transient body function requirements. It is certainly intended that such adaptations fall within the scope of the present invention. However, the following description is specifically directed to the adaptation of a microprocessor for use in an implantable cardiac pacer responsive to a circadian wake-sleep cycle.

Figure 1:
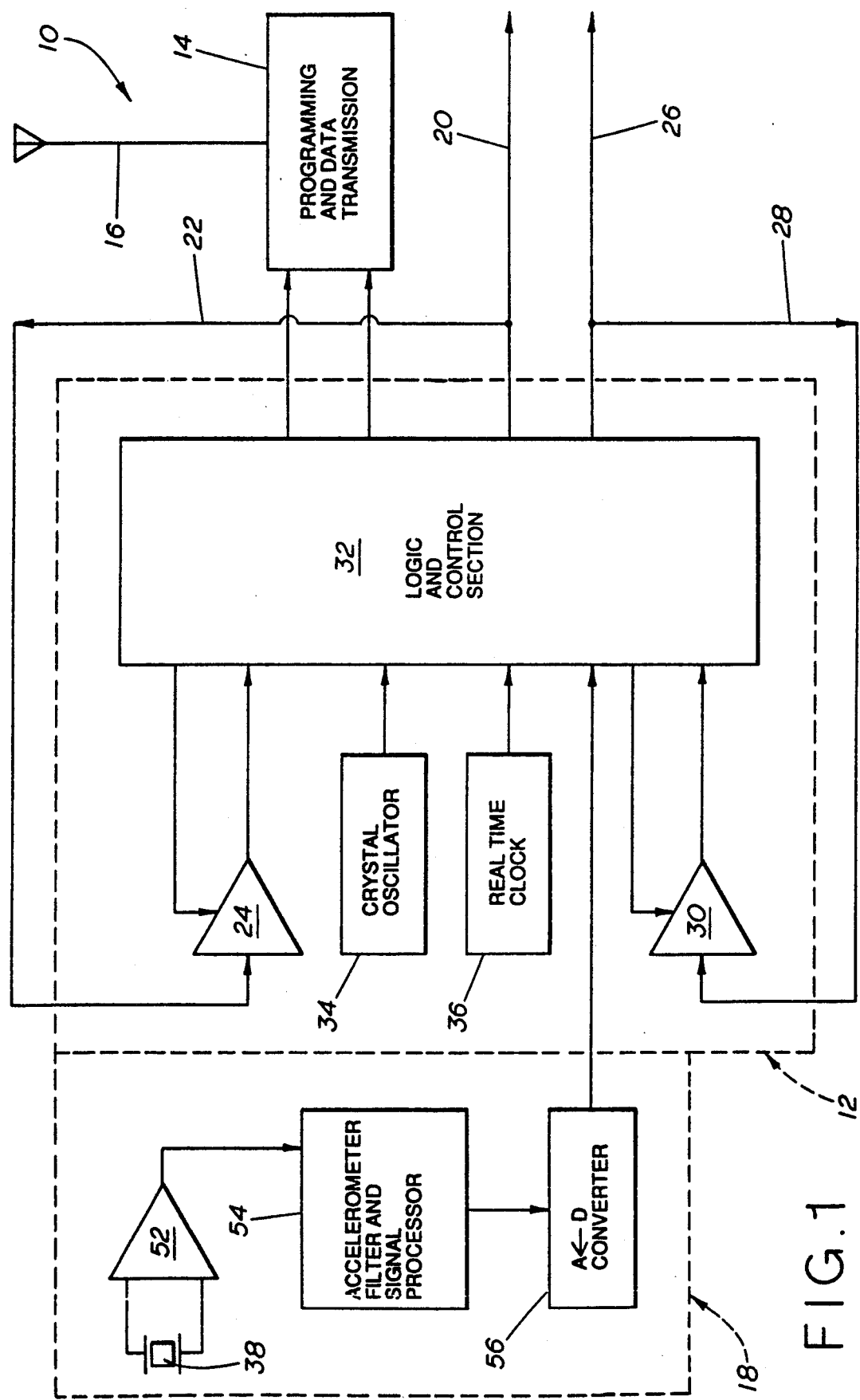
FIG. 1 is a block diagram illustrating basic interconnections between a microprocessor and an associated pacer.

Referring now to FIG. 1, there is depicted in block diagram circuitry comprising an implantable cardiac pacer 10. A microprocessor-based control circuit 12 receives data from selected sensors, exchanges data with other electronic devices and produces pulses or signals for regulating the heart. The control circuit 12 may transmit data to and receive data from a programming and data transmission circuit 14 adapted to receive instructions from time to time through an antenna 16 from an external source.

To operate in accordance with the principles of the present invention, the control circuit 12 must be provided with input from one or more sensors. In the illustrated embodiment, an accelerometer circuit 18 is illustrated as the preferred sensor. Those skilled in the art, however, will recognize that other sensors of events or conditions which can be correlated with physiologic needs may be selected without departing from the spirit or teachings of the present invention. As more fully described below, the control circuit 12 executes program steps to adjust the instantaneous output of the pacer 10, to compare the predicted physiologic requirements with input received from the sensors, such as accelerometer circuit 18, and to modify a logical model of projected circadian physiologic requirements.

The control circuit 12 produces a periodic electric signal for stimulating an atrial chamber of the patient's heart. The signal is then carried along a first lead 20 to a catheter implanted in or on the patient's heart. Between pulses produced by the pacer circuit 10, the electrical status of the heart is sampled through the first lead 20 and a first feedback line 22 to the control circuit 12. Such feedback signals are usually substantially weaker than the signals produced by the pacer 10 and are consequently amplified by a first sense amplifier 24. In the illustrated embodiment, the control circuit 12 will modify its commands to the pacer circuit 10 in response to the received feedback. This process is more fully described in U.S. Pat. No. 4,712,556 to Ross G. Baker, Jr., assigned to the same Assignee. The disclosure of that patent is incorporated herein by reference.

In a process similar to that described above in connection with atrial rates, the control circuit 12, in certain embodiments, may also produce periodic signal for stimulation of a ventricular chamber of the patient's heart. The signal is transmitted on a second lead 26 to a catheter lodged in the ventricle of the patient's heart. Again, the electrical status of the heart is periodically sensed along a second feedback line 28 and amplified by a second sense amplifier 30 as described above. Although a dual chamber pacer has been described, the present invention is equally applicable to single chamber pacemakers as well as other implantable devices.

The control circuit 12 comprises a logic and control section 32, which may be a microprocessor. A crystal oscillator 34 provides a periodic signal to the logic and control section 32, which signal is used to coordinate processes within the various circuits of the cardiac pacer 10. In the preferred embodiment, a signal derived from the crystal oscillator 34 by a conventional CMOS divider circuit is also input to a real time clock 36. The logic and control section 32 utilizes the output of the real time clock 36 to coordinate its logical model of projected cyclic physiologic requirements with actual elapsed time, as more fully described below.

Figure 7:
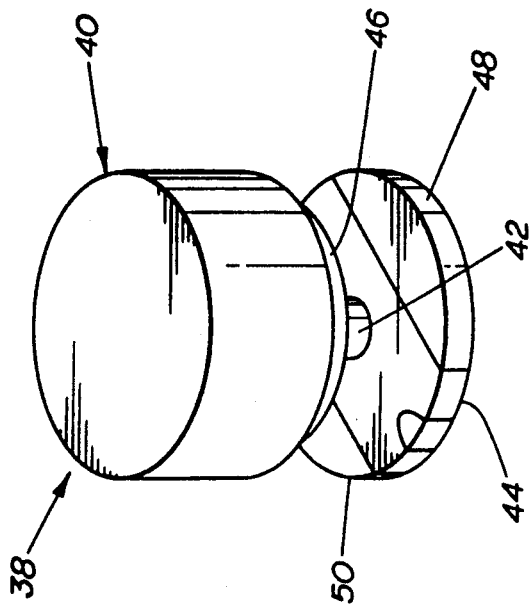
FIG. 7 is a perspective view of an accelerometer, which may be used in connection with the present invention.

In addition to input from the real time clock 36, the logic and control section 32 also receives input from sensors, such as accelerometer circuit 18. In the preferred embodiment, the accelerometer circuit 18 comprises a miniature piezoelectric accelerometer 38 available from Endevco. The piezoelectric accelerometer 38, shown in FIG. 7, comprises an inertial mass 40 mounted on a shaft 42. The shaft 42 is affixed to a base 44. Within the inertnal mass 40 is a piezoelectric material 46. The accelerometer 38 experiences accelerations as forces on the piezoelectric material 46. These forces produce electrical impulses in the piezoelectric material 46. Since the piezoelectric material 46 is electrically connected to a positive terminal 48 and a negative terminal 50 on the base 44, an electrical signal correlated to acceleration can be produced.

A charge amplifier 52 is used to amplify the output of the piezoelectric accelerometer 38. An accelerometer filter and signal processor 54 modifies the amplified signal from the charge amplifier 52. This may include, preferably, such conventional signal processors as a band-pass filter, a full wave rectifier, and a low-pass filter. In the preferred embodiment, a conventional band-pass filter may be used to select frequencies on the order of 0.5 Hz to 3.5 Hz. After full wave rectification, a low-pass filter would be employed to produce a signal proportional to the average acceleration present. The low-pass filter may attenuate waves having a period of less than sixty seconds. This tends to smooth output related to the phenomenon being detected by the accelerometer 38. The resulting output may then be sampled for amplitude during every pacing cycle. An analog-to-digital converter 56 changes the output signal of the accelerometer filter and signal processor 54 to digital form correlated to the average acceleration level detected by the accelerometer 38 and transmits the data to the logic and control section 32.

Figure 2:
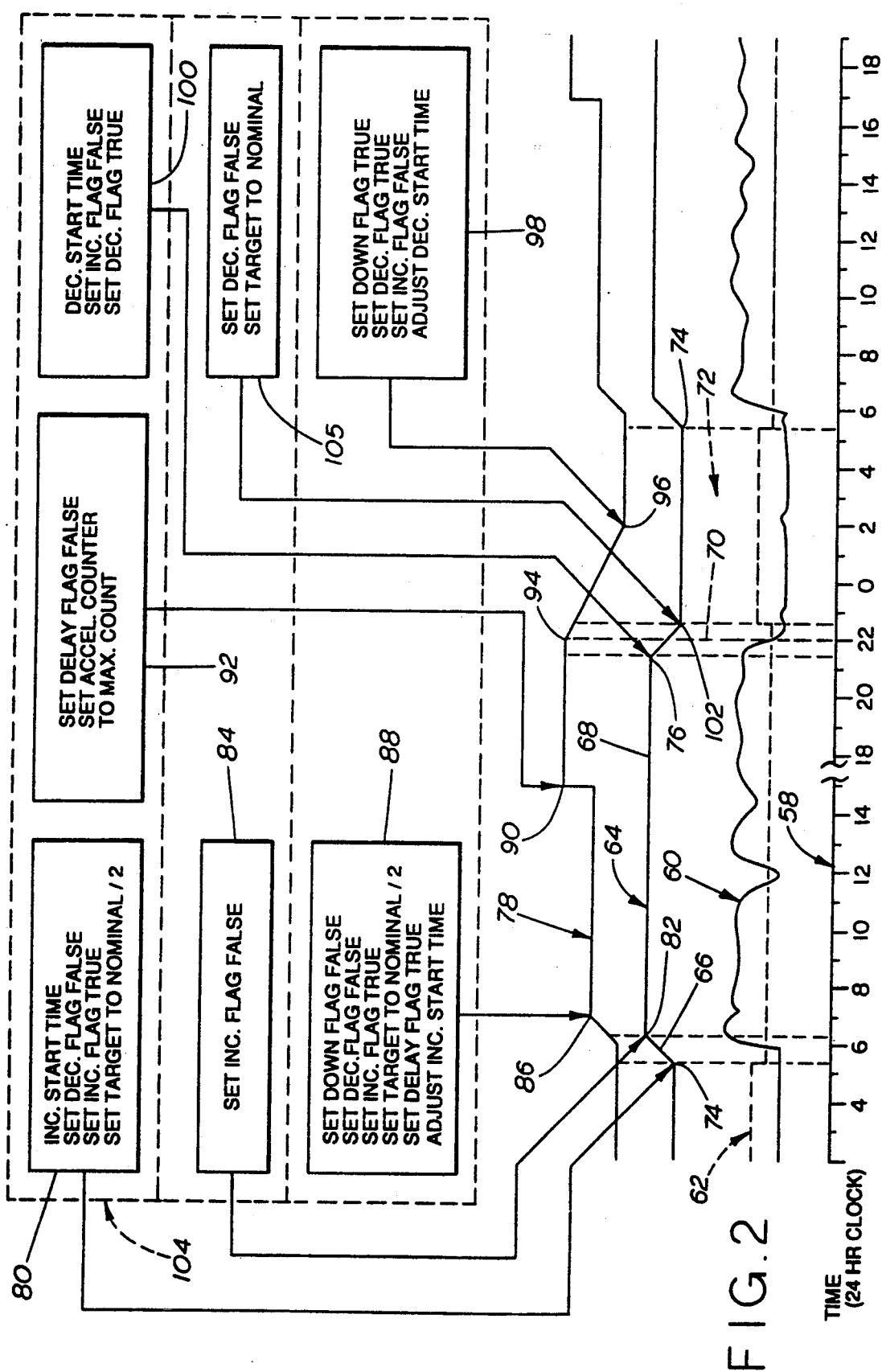
FIG. 2 is a graphical representation of exemplary values of selected parameters of the system for a selected period.

Before explaining the operation of a program routine for implementing this invention, a typical circadian cycle will be described. The chronological relationship between measured parameters, the predicted logical model of physiologic needs and the output of the pacer 10 will be explained with reference to FIG. 2. FIG. 2 graphically represents the status of various parameters effecting the implantable pacer 10 during a typical twenty-four hour cycle. FIG. 2 also shows representative times when selected important portions of the program routine (to be described below) are executed by the logic and control section 32.

A cyclic twenty-four hour scale 58 represents time of day, with zero being midnight. Above the scale 58, are four lines which represent parameters used or produced by the logic and control section 32. Acceleration sum 60 is a measured parameter derived from the output of the accelerometer circuit 18 and correlated to the activity of the patient. During the waking hours from six o'clock a.m. to about ten o'clock p.m. (22 on the scale) the magnitude of the acceleration sum 60 will be relatively high. During sleeping hours, the value of the acceleration sum 60 will be relatively low. Superimposed on the acceleration sum 60 is a dotted line representing a target value 62. The target value 62 is a programmable parameter which assumes different values during different times of the day. As will be explained more fully below, the magnitudes of the target value 62 and the acceleration sum 60 are compared in the process of adjusting the logical model of physiologic needs. FIG. 2 shows that the target value 62 is counter-cyclical when compared to the expected values of the acceleration sum 60. Thus, during a sleep period, only a relatively large value of the acceleration sum 60 will be deemed significant and effect the logical model, while during a waking period low values of the acceleration sum 60 will be deemed significant and will affect the logical model.

Line 64 illustrates an expected baseline heart rate to be controlled by the pacer 10. The current baseline heart rate is the minimum rate of pulses output by the pacer 10 to the heart. The baseline heart rate will increase during an increase period 66. The rate at which the change in baseline heart rate occurs is indicated by the slope of the line 64 during the increase period 66. During a waking period 68, the baseline heart rate is maintained at a selected level. Generally in the late evening, there is a decrease period 70 during which the heart rate is lowered to a lower level for a sleep period 72. The slope of the line 64 in the decrease period 70 is illustrative of the rate at which the change in baseline rate occurs. It will be recognized that the increase period 66 is not necessarily equal in duration to the decrease period 70. In the preferred embodiment, however, the decrease period 70 is equal to the increase period 66.

Neither an increase start time 74 nor a decrease start time 76 are fixed, since they must vary to adapt for change in activity because of such factors as changes in geography, season, legal time, work shifts, or habits of the patient. The line 64 represents a logical model of physiologic requirements which must be continually modified to adapt to changing circumstances.

Above the baseline heart rate line 64, there is a line representing the magnitude of an acceleration counter 78. The acceleration counter 78 is a parameter calculated by the logic and control section 32 to adjust the logical model for the next cycle. Its use will be explained more fully below.

The first significant event in a typical twenty-four hour cycle is usually the occurrence of the increase start time 74. In FIG. 2, this is shown as occurring at about 5:30 a.m. A test for initial conditions 80 will detect the appropriate time of day and set certain indicators, or flags. The baseline heart rate 64 will begin increasing, and the target value 62 will be reduced to a lower value, as shown. As the value of the acceleration sum 60 begins to increase above the target value 62 (which may occur before or after the increase start time 74), the acceleration counter 78 will begin to increase incrementally. If the acceleration sum 60 falls below the target value 62, the acceleration counter 78 will be incrementally decremented. About an hour after the increase start time 74, the baseline heart rate 64 will stop increasing at time 82. At time 82, an increment flag 84 is set to "false" and the pacer 10 will then maintain the patient's heart rate at at least this level until the decrease start time 76. The acceleration counter 78 will usually reach a target value at time 86 which corresponds to the patient being awake for about one hour. This time 86 may occur before or after the time 82 when the baseline heart rate 64 stops increasing. At time 86, post increase processing steps 88 will be executed to alter the status of the flags, including a flag to initiate a delay time during which no adjustments to the acceleration counter 78 are made. The time of day when time 86 occurs is used to adjust the logical model for the next cycle.

The next significant event shown in FIG. 2 occurs when a delay time has elapsed at time 90. At this time 90, another set of commands 92 is executed. A delay flag is set "false" and the acceleration counter 78 is set to to a maximum count. Thereafter, if the acceleration sum 60 falls below the target value 62, the acceleration counter 78 will be decremented, as is shown at time 94. If the acceleration sum 60 exceeds the target value 62, the acceleration counter 78 will be incremented, but it will not be permitted to exceed the maximum count. The acceleration counter 78 will continue to be decremented, based on the comparison between the acceleration sum 60 and the target 62, until a minimum value is reached at a time 96 (after about 4 hours have elapsed). At the time 96, post decrease processing commands 98 are executed. In particular, this set of commands uses the time of day when time 96 occurs to adjust the logical model for the next cycle.

Independent from the acceleration counter 78, the baseline heart rate 64 is maintained at a selected level until the decrease start time 76. At the decrease start time 76, decrease rate commands 100 are executed. In response to these commands, the baseline heart rate 64 is reduced incrementally to the selected level for sleep. At time 102, when the minimum level is reached, adjust rate commands 105 halt the decrease of the baseline heart rate 64 and adjust the target value 62.

In the next twenty-four hour period, the foregoing cycle is repeated except that, as will be explained, the increase start time 74 and the decrease start time 76 may be adjusted based on the times 86 and 96, among other factors.

Figure 3:
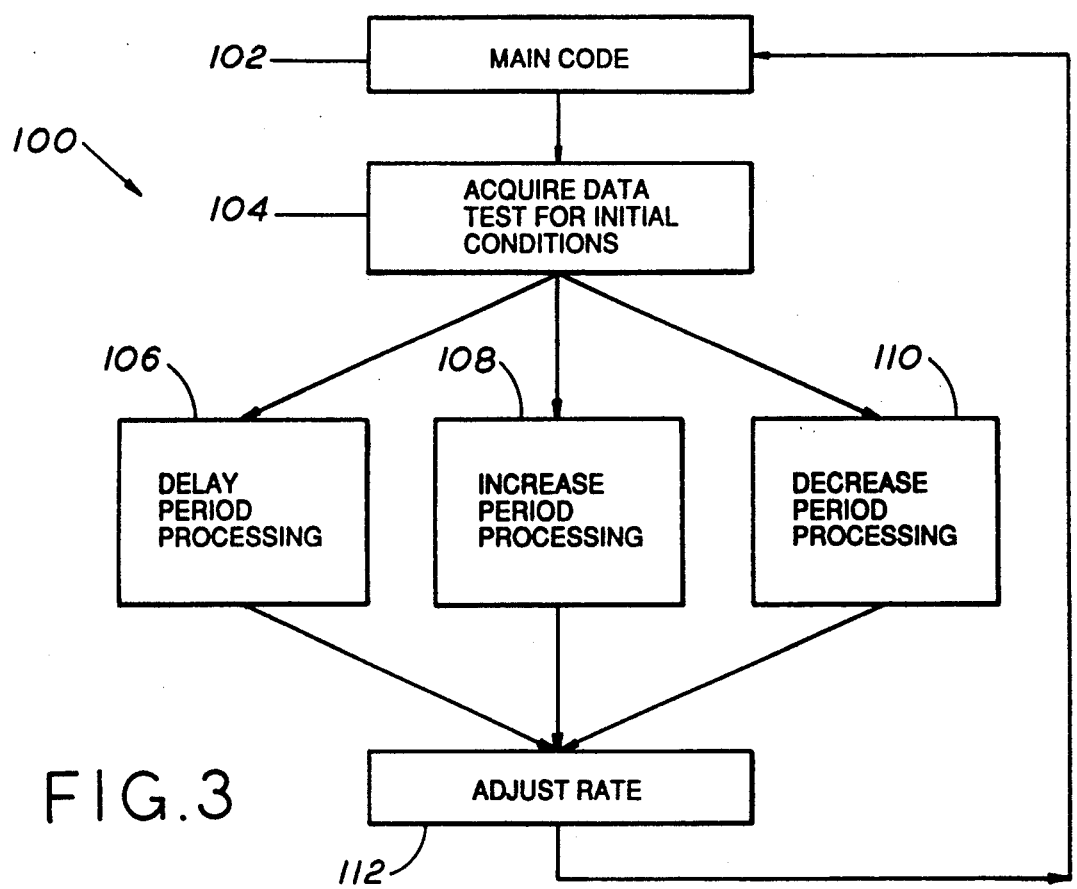
FIG. 3 is a functional block diagram of a system for responding to cyclic physiologic requirements.

A program for implimenting the invention will now be described in detail. Referring to FIG. 3, a program routine 100 is shown in block diagram. The logic and control section 32 uses the program routine 100 to maintain the logical model of a predicted circadian physiologic response cycle. In the preferred embodiment, the logic and control section 32 first executes various conventional algorithms associated with the cardiac pacer 10. The conventional algorithms are herein designated as main code 102. In addition, the logic and control section 32 will periodically accumulate data from the accelerometer circuit 18 and will test 104 the real time clock 36 for the predicted start time of a cyclic change in physiologic requirements, such as either increase start time 74 or decrease start time 76. After a start time has been detected by the test 104, the logic and control section 32 will increase or decrease the heart rate, depending on the type of start time detected. The logic and control section 32 will periodically monitor the level of events detected by the sensors, such as accelerometer circuit 18. When data has been acquired, the logic and control section 32 will test for the existence of one of three conditions, and will branch to selected parts of the program 100 if any of the three conditions are detected.

The three conditions are delay period, increase period and decrease period. Detection of the delay period initiates delay period processing 106; increase period processing 108 follows detection of the increase period; and decrease period processing 110 follows detection of the decrease period. Each of these conditions and the associated processing will be more completely described below. During each operation cycle of the logic and control section 32, the logic and control section 32 adjusts 112 the rate being produced by the cardiac pacer 10 for stimulation of the patient's heart, if required.

Figure 4A:
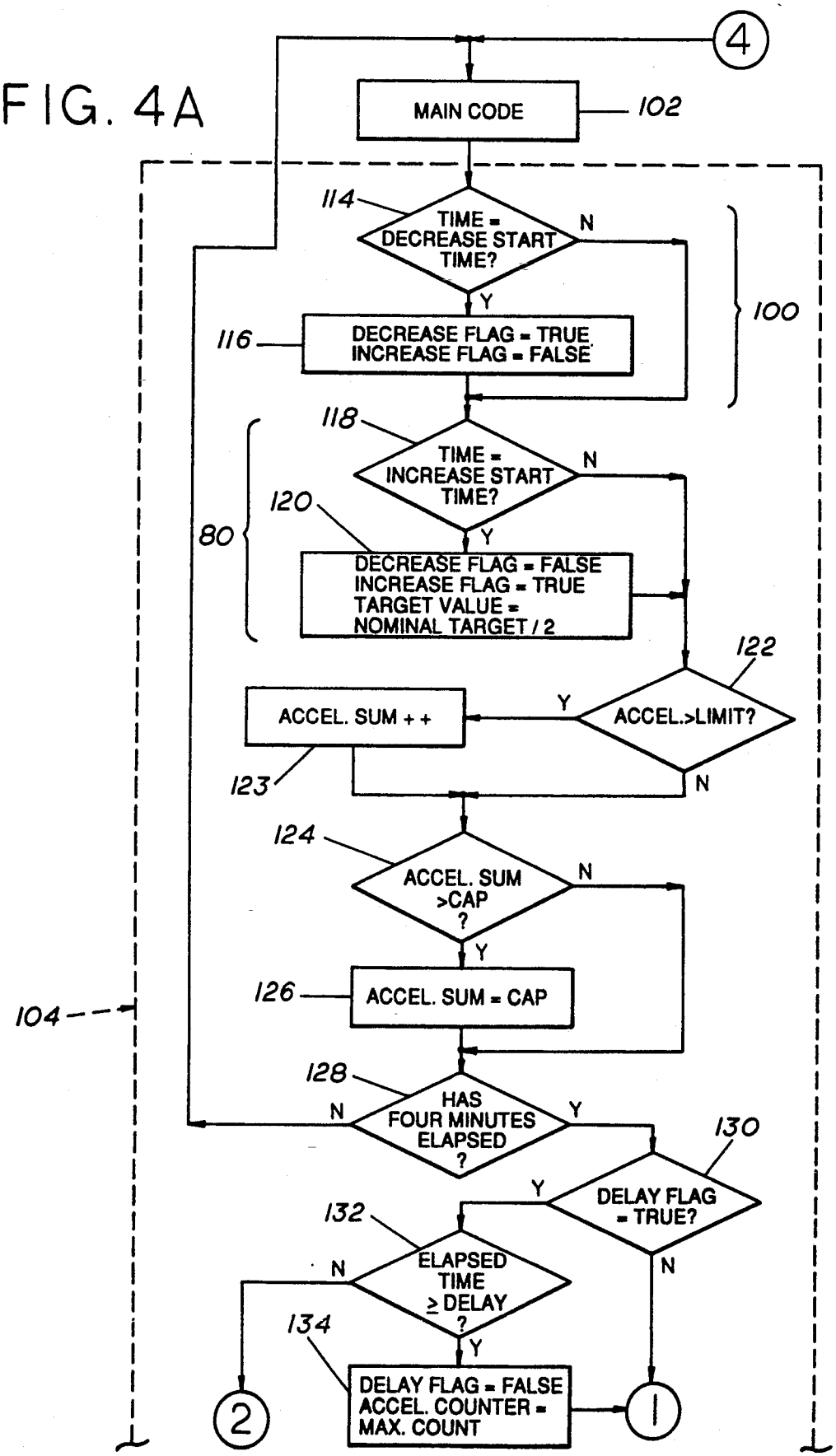
FIG. 4A is a first part of a flow diagram of the system.
Figure 4B:
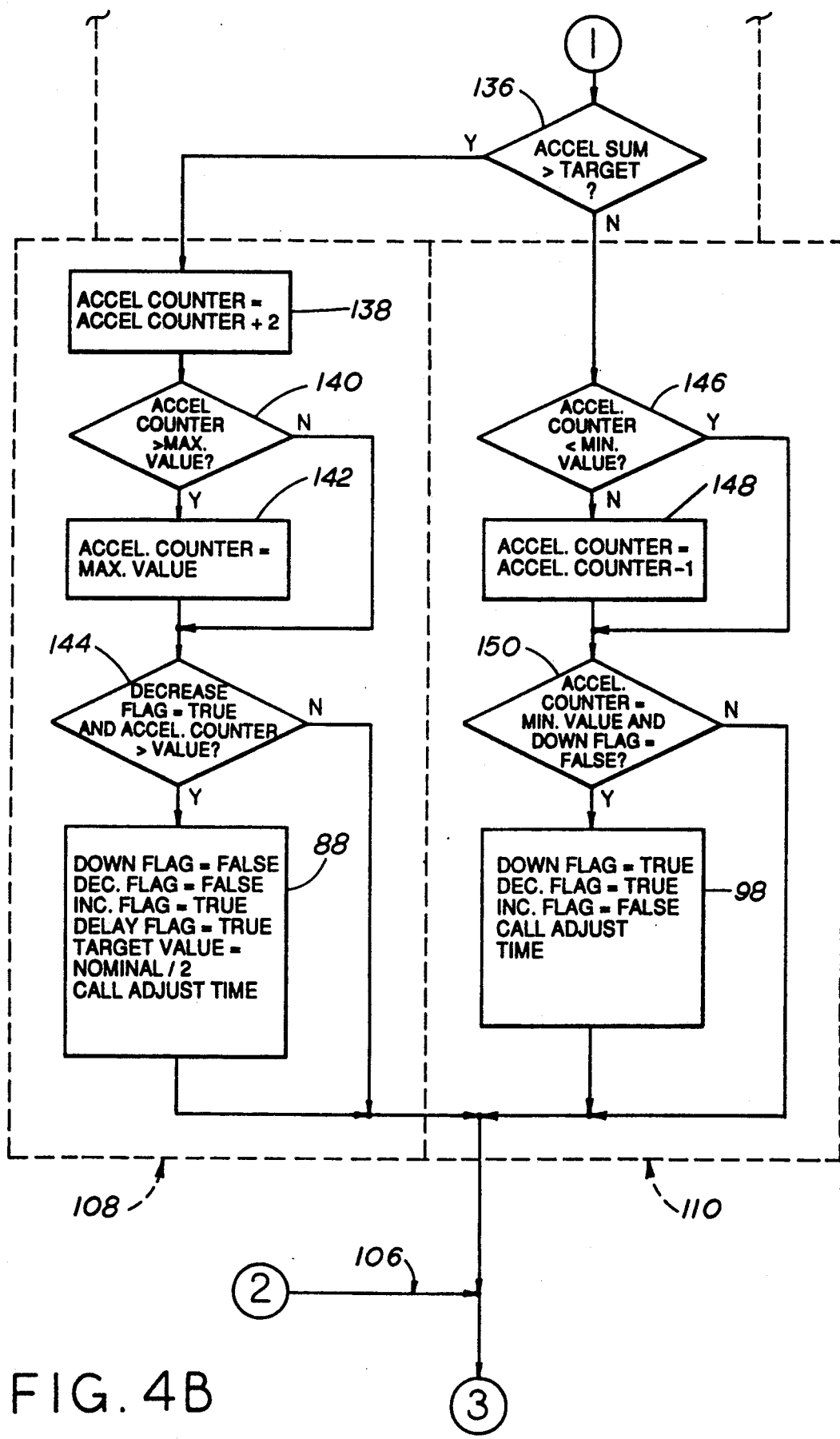
FIG. 4B is a second part of the flow diagram of the system.
Figure 4C:
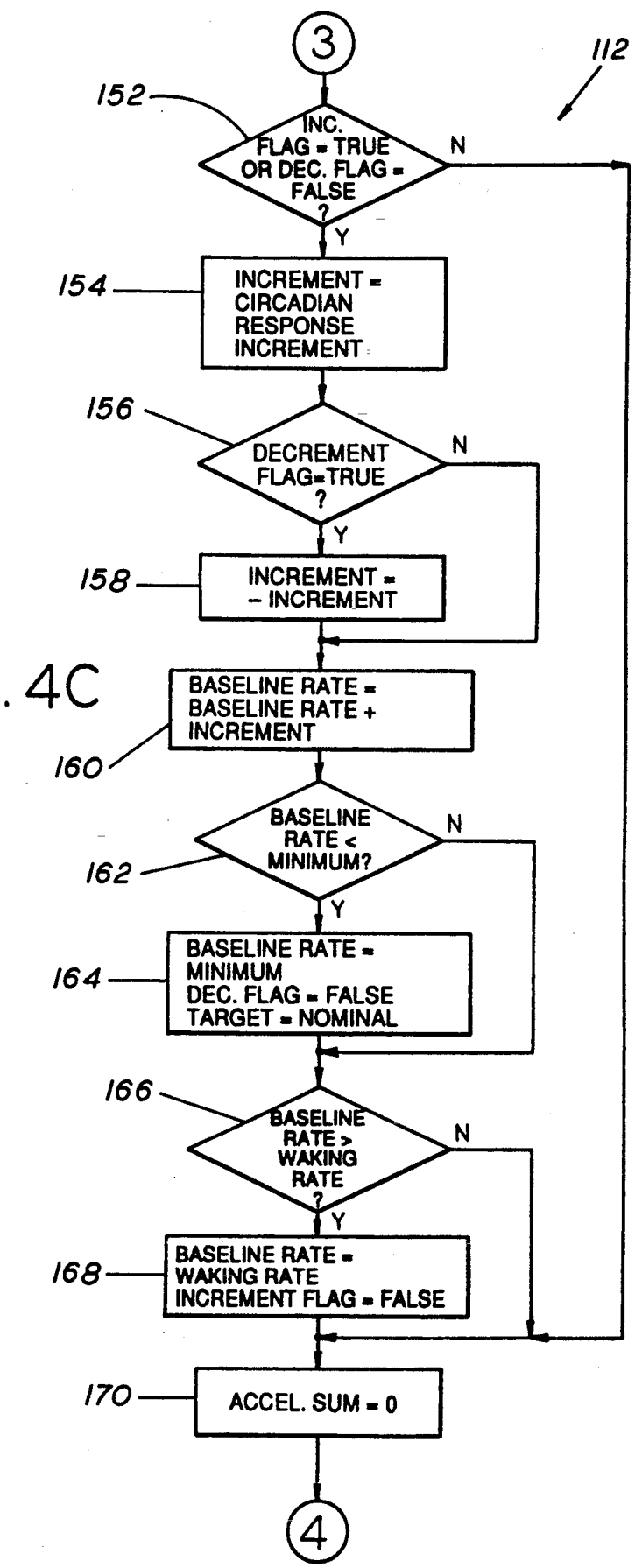
FIG. 4C is a third part of the flow diagram of the system.
Figure 4:
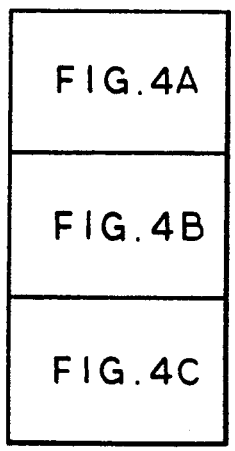
FIG. 4 shows the relationship between FIG. 4A, FIG. 4B and FIG. 4C.

The foregoing sequence is more fully described hereafter in connection with FIG. 4, which is a flow diagram of an algorithm to be implemented by the logic and control section 32. Within the cardiac pacer 10, the logic and control section 32 cycles substantially continuously through a code sequence associated with the regulation of pulses to a patient's heart. To the extent that such programming is not unique to the present invention, it is represented in FIG. 4 by the main code 88. During each operation cycle, the logic and control section 32 acquires data and tests 104 for initial conditions. To do this, the logic and control section 32 samples the output of the real time clock 36 and compares 114 the time to a predetermined value for the decrease start time 76 to begin decreasing the rate of pulses transmitted to the heart. If the real time and the predetermined decrease start time 76 are equal, a decrease flag is set 116 to "true" and an increase flag is set to "false". The time is then compared 118 to a predicted increase start time 74 to begin to increase the rate. If the real time and the increase start time 74 are equal, the decrease flag is set 120 to "false", the increase flag is set "true", and the target value 62 is scaled to a nominal target value divided by a constant, such as two.

The logic and control circuit 32 then samples 122 the accelerometer circuit 18 and compares the digital output of the accelerometer circuit 18 to a limit. If the digital output of the accelerometer circuit 18 is above the limit, an acceleration sum 60 is incremented 123. The acceleration sum 60 is then compared 124 to a cap, or maximum predetermined value. If the acceleration sum exceeds the cap, the acceleration sum is set 126 equal to the cap.

Using the real time clock 36, the logic and control section 32 then checks 128 for a predetermined elapsed time. In the preferred embodiment, four minutes, plus or minus eight seconds, has been selected for the elapsed time. If the predetermined elapsed time has not elapsed, program control returns to cycle through the main code 102 once again. If the predetermined period has elapsed, the status of a delay flag is checked 130. The delay flag is set at time 86 after the acceleration counter 78 has increased and remains set for a predetermined period on the order of eleven hours. The delay flag is used to prevent the logic and control circuit 32 from erroneously identifying a morning or afternoon nap as the beginning of a nightly sleep period. If the delay flag is "true", the logic and control section 32 compares 133 the elapsed time since the delay flag was set to "true" to a predetermined delay value. If more time has elapsed than the predetermined delay value, the delay flag is set 134 to "false" and the acceleration counter 178 is set to a preselected maximum counter value.

In the preferred embodiment, the acceleration counter 78 will be incremented or decremented depending on the value of the acceleration sum 60 accumulated during the four minute cycle. If the patient lies down to go to sleep at about time 94, only a small number of accelerations will be detected by the accelerometer circuit 18 during any four minute period. The acceleration counter 78 will be continually decremented, as will be more fully explained below, and the decrease start time 76, for the next day, will not be changed. If, however, substantial accelerations are detected during a number of four minute periods, the ending time 96 will be different from expected and the decrease start time 76 will be changed. Similarly, accelerations are expected during the increase period 66, and if a sufficient number of accelerations are not detected or if the accelerations begin to occur earlier than expected, the increase start time 74 and decrease start time 76 will be adjusted, as explained below.

Preparatory to adjusting the increase start time 74 or the decrease start time 76, the acceleration sum 60 is compared 136 to the target value 62. If the target value 62 is exceeded, the acceleration counter 78 is incremented 138. In the preferred embodiment, the acceleration counter 78 is incremented by two. The acceleration counter 78 is then compared 140 to a maximum value. If the acceleration counter 78 exceeds the maximum value, the acceleration counter 78 is set 142 equal to the maximum valve. If the down flag tests 144 "true" and the acceleration counter is greater than a selected value, post increase processing 88 is commenced. In the post increase processing 88 the down flag is set to "false", the decrease flag is set to "false", the increase flag is set to "true", the delay flag is set to "true", the target value is set to one half of the nominal target value, and an adjust time subroutine is called. The adjust time subroutine adjusts the predicted increase start time 74 and the predicted decrease start time 76 for the next circadian cycle within selected maximum and minimum limits.

Returning now to the step of comparing 136 the acceleration sum 60 to the target value 62, if the acceleration sum 60 does not exceed the target value 62, the acceleration counter 78 is compared 146 to a minimum value, for example, zero. If the acceleration counter 78 is greater than the minimum value, the acceleration counter 78 is decremented 148. In the preferred embodiment, the acceleration counter is decremented by one. The logic and control section 32 then tests 150 if the acceleration counter 78 is equal to the minimum value and if the down flag is "false". If both these conditions are met, post decrease processing 98 takes place. The post decrease processing 98 comprises setting the down flag to "true", setting the decrease flag to "true" and setting the increase flag to "false" and calling the adjust time subroutine.

The logic and control section 32 will next proceed to implement the adjust rate processing 112. In these steps it is first determined 152 if either the increase flag or the decrease flag is "true". If either of these conditions is met, an increment variable is set 154 to a programmable circadian response increment. If the decrement flag is "true" 156, the sign of the increment is changed 158 from positive to negative. The value of the increment, positive or negative, is then added 160 to a value of the baseline rate 68. The resulting baseline rate 68 is compared 162 to a minimum rate. If the baseline rate 68 has fallen below the minimum rate, the baseline rate 68 is set 164 equal to the minimum rate and the decrement flag is set to "false". The target 62 for the acceleration sum 60 is reset to the nominal target value. The baseline rate 68 is then compared 166 to a waking rate. If the waking rate has been exceeded, the baseline rate 68 is set 168 equal to the waking rate and the increment flag is set to "false". The acceleration sum is reset 170 to zero and program control is returned for another pass through the main code 102 and the routines which have been described above.

Figure 5:
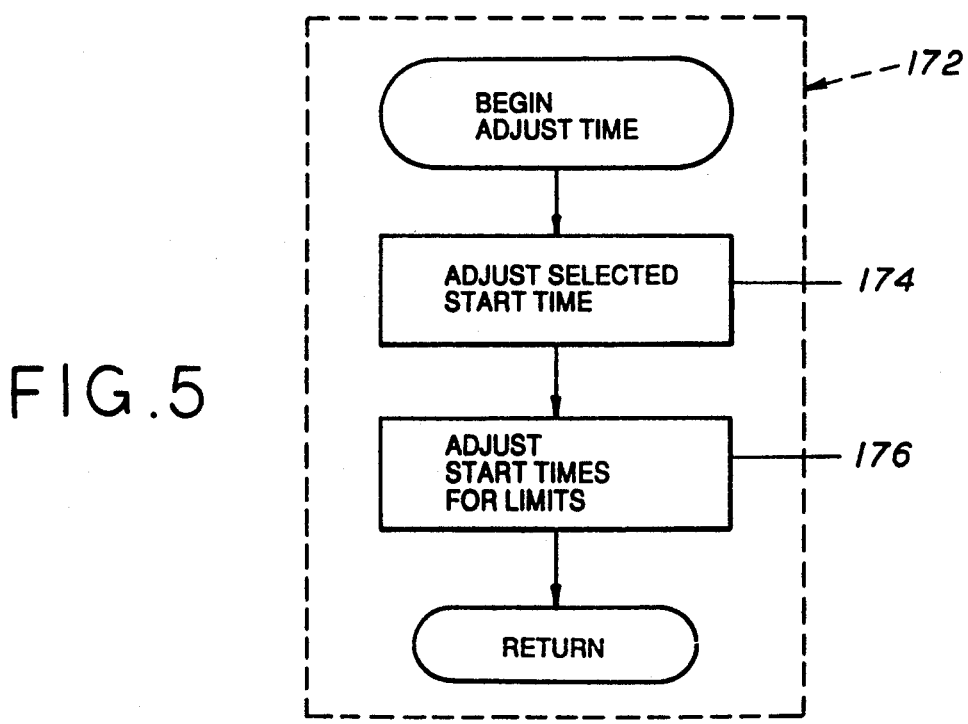
FIG. 5 is a functional block diagram of a subroutine from the flow diagram of FIG. 4B.
Figure 6A:
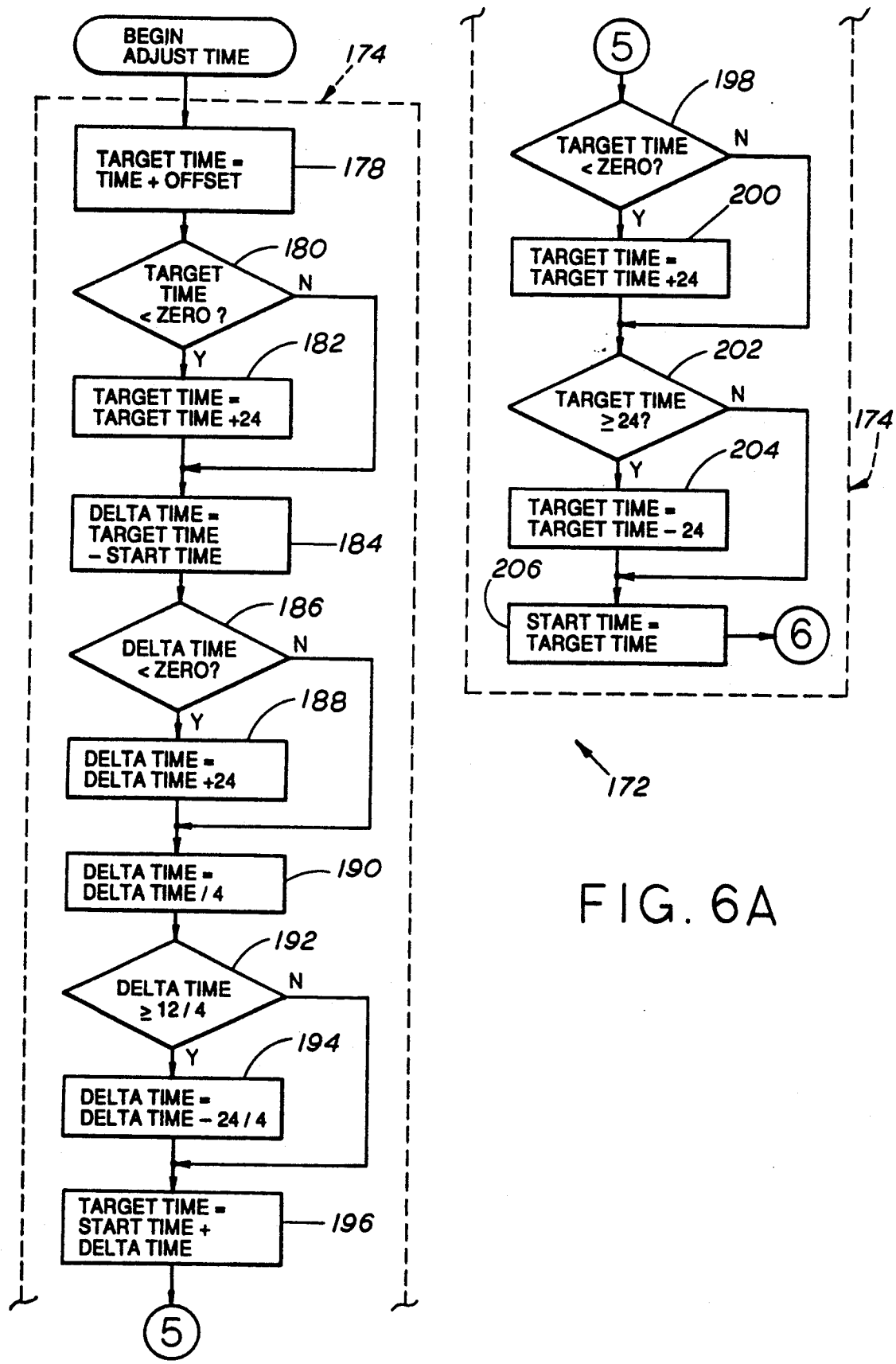
FIG. 6A is a first part of a flow diagram of the subroutine of FIG. 5.
Figure 6B:
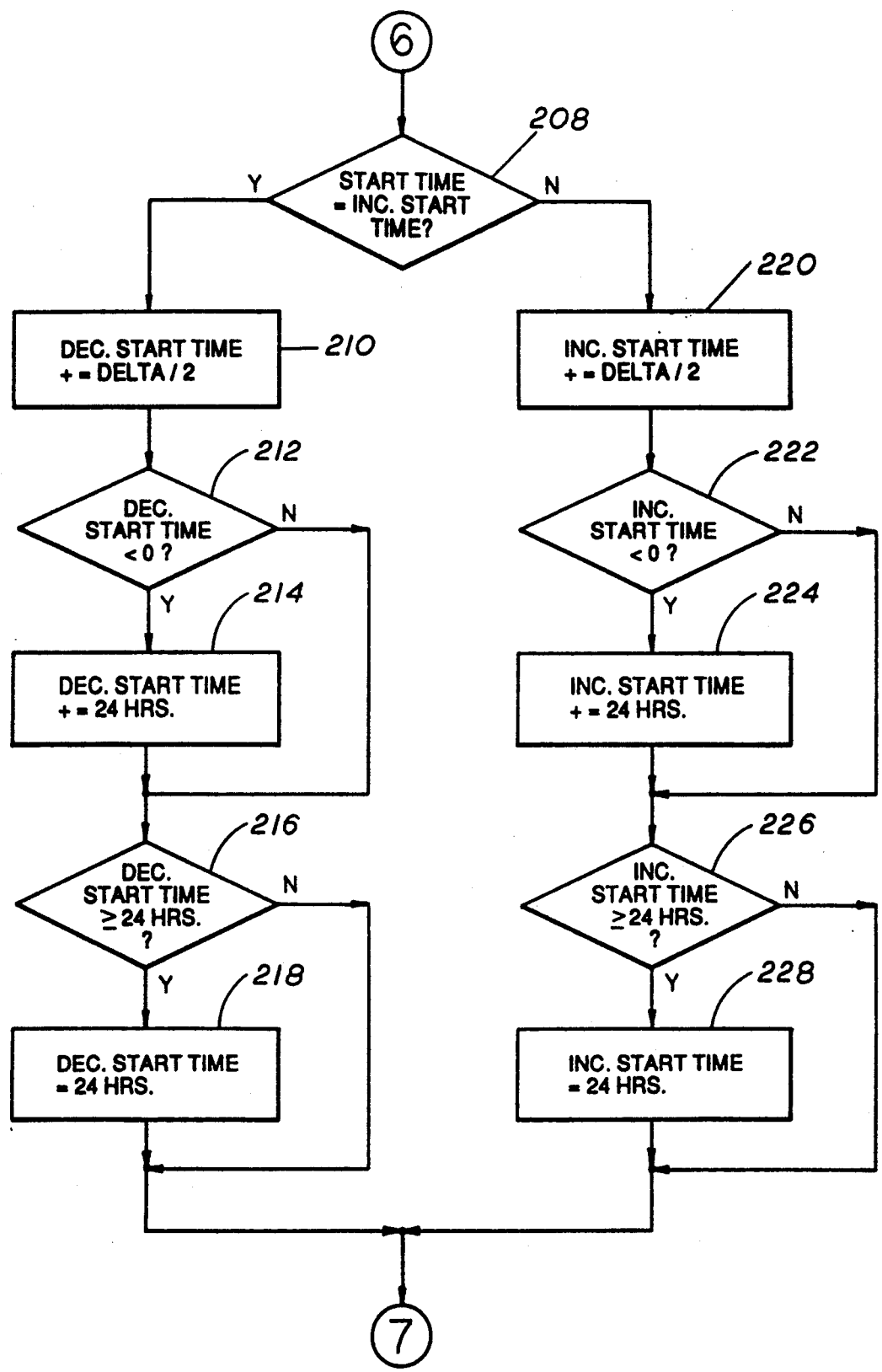
FIG. 6B is a second part of the flow diagram of the subroutine of FIG. 5.
Figure 6C:
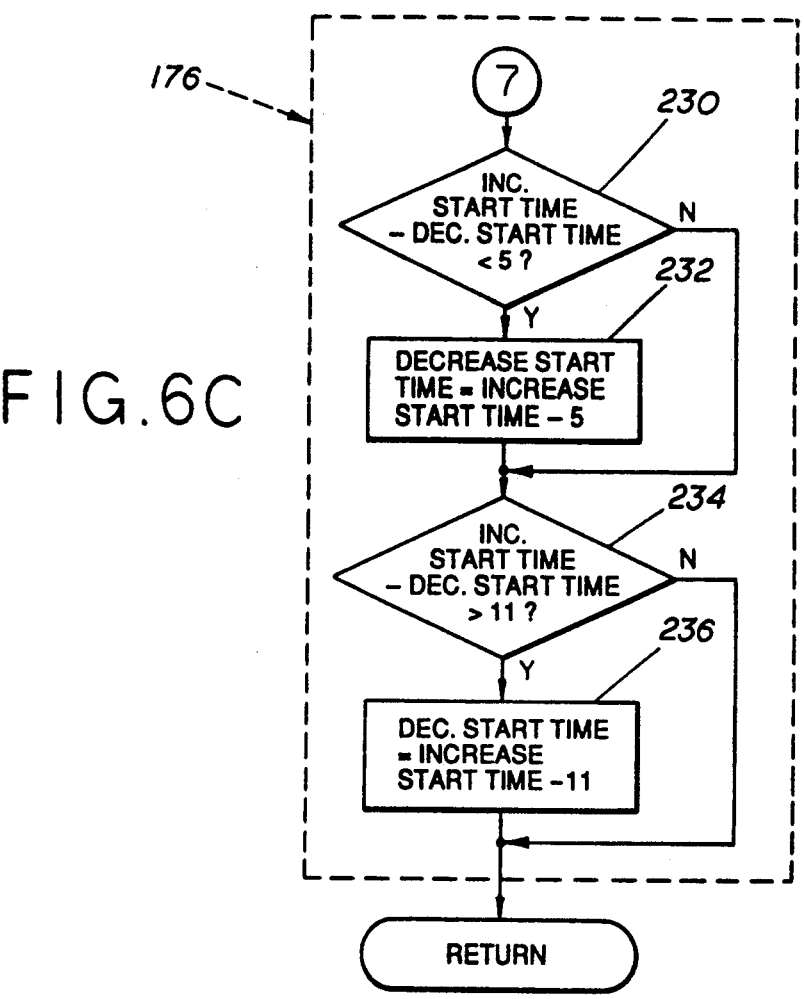
FIG. 6C is a third part of the flow diagram of the subroutine of FIG. 5.
Figure 6:
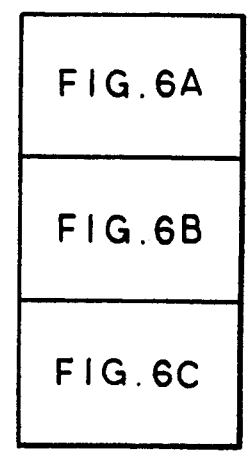
FIG. 6 shows the relationship between FIG. 6A, FIG. 6B and FIG. 6C.

Reference is now made to FIG. 5 and FIG. 6 for a description of an adjust time subroutine 172. In FIG. 5, a functional block diagram of an appropriate subroutine is disclosed. When the subroutine 172 is invoked, a selected start time, such as either the increase start time 74 or the decrease start time 76, is adjusted 174 in accordance with a new predicted start time based on detected accelerations and the start time for the last cycle. A new start time is computed. When the new start time (for example, the increase start time 74) has been computed, the other start time (for example, the decrease start time 76) is adjusted based on the change from the selected start time to the new predicted start time. This adjustment occurs in the current circadian cycle so that a predicted change in one start time has an immediate effect on the next succeeding start time. The expected elapsed time between the decrease start time 76 and the increase start time 74 is then examined 176 and the decrease start time is adjusted so that there will be a sleep period 72 having a duration within a predetermined minimum and maximum range.

Reference is now made to FIG. 6, wherein a flow diagram of the subroutine 172 for adjusting start times is disclosed. The logic and control section 32 obtains the current time from the real time clock 36 and offset, a variable, is added 178 to the time to obtain a target time. The target time represents the expected increase or decrease start time based on the presence or absence of accelerations. In the case of the decrease start time (in the preferred embodiment) the offset is set equal to negative five hours. For the increase start time, offset is set equal to negative 1.75 hours.

The real time clock 36 gives time values from zero to twenty-four and then repeats. All computed values, therefore, must fall within the range from zero to twenty-four. The target time is therefore compared 180 to zero, and if the target time is less than zero it is adjusted to within the mentioned range by adding 182 twenty-four to the target time. The difference between the target time and the start time, either the increase start time 74 or the decrease start time 76, is assigned 184 to delta time. Delta time represents the change in start time from the present start time to the next predicted start time, based solely on the occurrences of accelerations. Delta time is compared 186 to zero and if delta time is less than zero, it is adjusted to fall within the range of zero to twenty-four by adding 188 twenty-four. The magnitude of the delta time variable is then reduced 190 by a damping factor or time constant. The damping factor tends to prevent the logic and control section 32 from oscillating in fixing start times in response to varying acceleration conditions. In response to a change in wake/sleep patterns, a patient's heart rate and metabolism tends to slowly adjust to the new pattern under the control of the cardiac pacer 10, just as a healthy person gradually adjusts to changes in wake/sleep patterns. In the preferred embodiment, delta time is reduced to one-fourth its original value.

The logic and control section 32 selects the minimum of the difference of the start time less the target time or the difference of the target time less the start time. By selecting the minimum difference, changes in the logical model from one circadian cycle to the next are minimized and the model is adjusted to major changes in fewer cycles. The logic and control section 32 next reduces the selected minimum difference by the damping factor. In the present embodiment, this limits the variation to not more than three hours per day. Thus, the reduced delta time is compared to three (twelve divided by four) in step 192. If the adjusted delta time is greater than or equal to three, six is subtracted from the delta time and is assigned to delta time at step 194. Because of the range limits imposed on delta time in the preceding processes, this step 194 has the effect of bringing delta time to within the range negative three hours to positive three hours.

The target time is assigned 196 a value equal to the start time used in the present cycle (either the decrease start time 76 or the increase start time 74) plus delta time, as computed above. The new target time is then compared 198 to zero. If the target time is less than zero, twenty-four hours is added 200 to the target time, to bring the target time within the range zero to twenty-four. The target time is next compared 202 to twenty-four hours and if the target time is greater than or equal to twenty-four hours, twenty-four is subtracted 204 from the target time to bring the target time within the range zero to twenty-four. With these adjustments, the start time is then assigned 206 the value of the target time. This sets the new start time for the next cycle.

If a first start time (for example, the increase start time 74) is to be changed for the next cycle, the intervening start time (for example, the decrease start time 76) is also expected to change. A prospective adjustment is made, therefore, equal to one-half the change (delta) made to the first start time. The logic and control section 32 determines 208 which start time is being changed. If the increase start time 74 is being changed, the decrease start time 76 is changed 210 by adding one-half delta. The resulting decrease start time 76 is then brought within the range of zero to twenty-four by testing 212 for a value less than zero and, if such a value is detected, adding 214 twenty-four to the decrease start time 76, and then testing 216 for a value greater than or equal to twenty-four and, if such a value is detected, subtracting 218 twenty-four from the decrease start time 76. If the decrease start time 76 is being changed, the increase start time 74 is changed 220 by adding one-half delta. The resulting increase start time 74 is then brought within the range of zero to twenty-four by testing 222 for a value less than zero, and, if such a value is detected, adding 224 twenty-four to the increase start time 74, and then testing 226 for a value greater than or equal to twenty-four and, if such a value is detected, subtracting 228 twenty-four from the increase start time 74.

Since a new start time, which may either be the decrease start time 76 or the increase start time 74, has been assigned, the limits of these start times must be adjusted 176, as mentioned above. The logic and control section 32 checks 230 to see if the projected elapsed time from the decrease start time 76 to the increase start time 72 is less than five hours. If the difference is less than five hours, the decrease start time 76 is adjusted 232 to be five hours before the increase start time 72. In the preferred embodiment, the increase start time 72 is held fixed and the decrease start time 76 is adjusted. The logic and control section 32 then checks 234 if the decrease start time 76 is more than eleven hours before the increase start time 72. If this condition exists, the decrease start time 76 is set 236 to be eleven hours before the increase start time 82. The result of the aforementioned two checks 230 and 234 is that the patient will have a predicted sleep period, with its associated reduced cardiac pace rate, which is within maximum and minimum limits.

Figure 8:
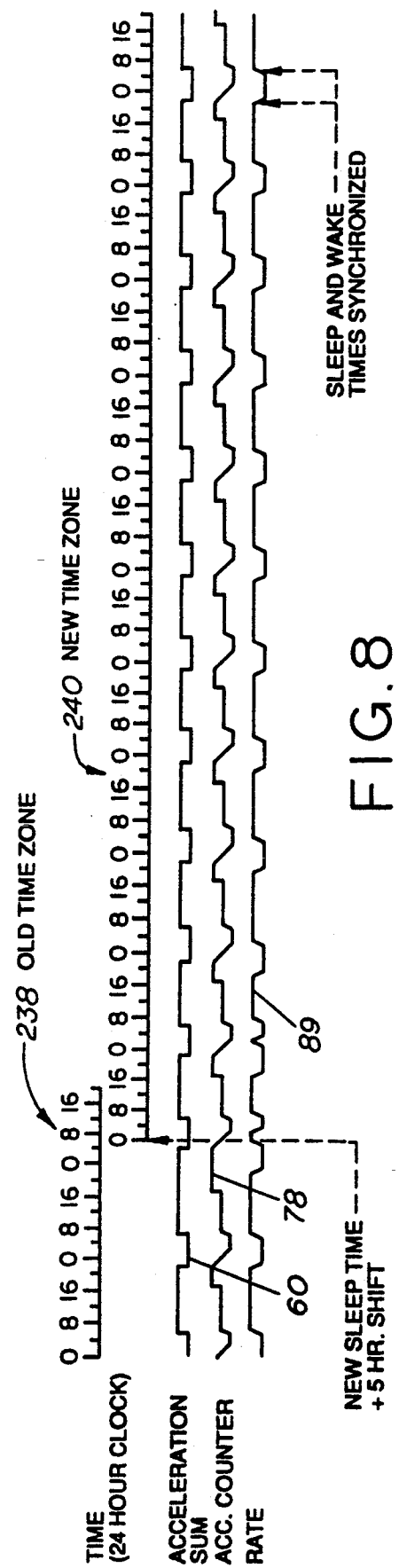
FIG. 8 is a graphical representation of exemplary values of selected parameters of the system over a period of days.

An example of the pacer's adjustment to new conditions is illustrated in FIG. 8. In FIG. 8 two cyclic twenty-four hour scales are shown. A first scale 238 represents an old time zone to which the patient is assumed to be accustomed. If the patient moves to a new time zone, represented by scale 240, there will be an adjustment in his circadian rhythm based on his new pattern of activity. The new pattern of activity is represented by the acceleration sum 60. The change in activity is reflected in the acceleration counter 78. The acceleration counter 78 in turn effects the baseline heart rate 64. When the patient moves to the new time zone 240, some relatively abrupt changes in the baseline heart rate 64 will be observed. Because of damping (explained above in connection with the adjust time subroutine 172), the baseline rate 64 will gradually and asymptotically become synchronized with the new time zone over a period of days.

The operations explained above may be further understood by reference to the following pseudo code program. The syntax of the pseudo code is derived for the C programming language. Of course, other machine specific languages, such as assembler, may be chosen to implement the invention without departing from the teachings of the invention.

```
CIRCADIAN_RESPONSE( )
{
    int mtimer;
    int delta, delta_t;
/* set mtimer to the value of the real time clock */
    mtimer = timer;
    if (mtimer = dec_start_time)
    {
        dec_flag=true;
        inc_flag=false;
    }
    if (mtimer = inc_start_time)
    {
        inc_flag=true;
        dec_flag=false;
        target = nominal_target/2;
    }
    if (accel_now > limit)
    {
        accel_sum ++;
        if (accel_sum > cap)
            accel_sum = cap;
    }
/* Have four minutes, elapsed? */
    if (mtimer—last_time>4_minutes)
    {
/* Check to see if time to turn off the delay flag and */
/* start checking for sleep. */
        if (delay_flag)
        {
/* Calculate elapsed time */
            if (timer < delay_start_time)
                delay_start_time -= _24_HOURS;
            elapsed_time = timer − delay_start_time;
            if (elapsed_time >= delay_time)
            {
                delay _flag = false;
                accel_counter = 64;
            }
        }
/* Is delay time over? Is activity present? */
        if (delay_flag = false)
        {
            if (accel_sum > target)
            {
                accel_counter += 2;
                if (accel_counter > 64)
                    accel_counter = 64;
/* Is waking detected? */
                if (down_flag and accel_counter>32)
                {
                    down_flag = false;
                    dec_flag = false;
                    delay_flag = true;
                    inc_flag = true;
                    delay_start_time = timer;
                    target = nominal_target /2;
                    ADJUST_START_TIME(start_time,-1.75_HRS);
                }
            }
            else
            {
                if (accel_counter != 0)
                    accel_counter—;
/* Is sleep detected? */
                if (accel_counter = 0 and not down_flag)
                {
```

```
                down_flag = true;
                dec_flag = true;
                inc_flag = false;
                ADJUST_START_TIME(start_time, −5_HRS);
            }
        }
    }
    if (dec_flag or inc_flag)
    {
        if (dec_flag)
            baseline_rate −= natural_adjustment;
        else
            baseline_rate += natural_adjustment;
        if (baseline_rate < min_rate)
        {
            baseline_rate = min_rate;
            dec_flag = false;
            target = nominal_target;
        }
        else if (baseline_rate > ref_rate)
        {
            baseline_rate = ref_rate;
            inc_flag = false;
        }
    }
    accel_sum = 0;
    last_time = timer;
    }
}
ADJUST_START_TIME(start_time, offset)
int offset;
int *start_time;
{
    int target_time;
    int delta;
    target_time = offset + timer;
    if (target_time < 0) target_time += _24_HOURS;
    delta = target_time − *start_time;
    if (delta < 0) delta += _24_HOURS;
    delta = delta/4;
    if (delta >= _12_HOURS/4) delta −= _24_HOURS/4;
    target_time = delta + *start_time;
    if (target_time < 0) target_time += _24_HOURS;
    if (target_time >= _24_HOURS) target_time −= _24_HOURS;
    *start_time = target_time;
    if (start_time = &_inc_start_time)
    {
        dec_start_time += delta/2;
        if (dec_start_time < 0) dec_start_time += _24_HOURS;
        if (dec_start_time >= 24) dec_start_time −= _24_HOURS;
    }
    else
    {
        inc_start_time += delta/2;
        if (inc_start_time < 0) inc_start_time += _24_HOURS;
        if (inc_start_time >= 24) inc_start_time −= _24_HOURS;
    {
/* Check to see if the difference between inc_time and */ /*
dec_time is between 11 and 5 hours. */
    delta = inc_start_time − dec_start-time;
    if (delta < 0)
        delta += _24_HOURS;
    if (delta < _5_HOURS)
    {
        dec_start_time = inc_start_time − _5_HOURS;
        if (dec_start_time < 0)
            dec_start_time += _24_HOURS;
    }
    if (delta > _11_HOURS)
    {
        dec_start_time = inc_start_time − _11_HOURS;
        if (dec_start_time < 0)
            dec_start_time += _24_HOURS;
    }
}
```

The invention may be embodied in other specific forms without departing from the spirit or essential characteristics thereof. The present embodiment is therefore considered in all respects as illustrative and not restrictive, the scope of the invention being indicated by the appended claims rather than by the foregoing description, and all changes which come within the meaning and range of equivalency of the claims are therefore intended to be embraced therein

What is claimed and desired to be secured by U.S. Letters Patent is:

1. An implantable body function assistance device comprising:
    means for influencing a body function of a patient;
    means for sensing a parameter correlated to physiologic needs;
    means for producing a predictive model of cyclic physiologic needs, the model comprising a plurality of periods, each period having a predicted duration and a predicted minimum physiologic need;
    memory means for storing said predictive model
    real time clock means synchronized with a diurnal cycle;
    control means interconnecting the influencing means, the clock means, and the model producing means for controlling the output of said influencing means responsive to the model producing means and the clock means; and
    means for modifying the model maintained by the memory means responsive to the sensing means and the real time clock means.

2. An implantable body function assistance device according to claim 1 wherein the control means further comprises means for controlling the output of said influencing means responsive to the model maintaining means, the sensing means, and the clock means.

3. An implantable body function assistance device according to claim 1 or claim 2, wherein the model modifying means further comprises means for adjusting the predictive model responsive to prior status of the model.

4. An implantable body function assistance device according to claim 3, wherein the adjusting means further comprises means for damping the adjustment of the predictive model.

5. An implantable body function assistance device according to claim 4, wherein the adjusting means are responsive to the prior status of the model in one preceding duration of time represented by the model.

6. An implantable body function assistance device according to claim 5, wherein the cyclic physiologic needs are circadian physiologic needs associated with a wake/sleep cycle.

7. An implantable body function assistance device according to claim 1 or claim 2, wherein the model modifying means further comprise means for limiting the duration of at least one period of the predictive model.

8. An implantable body function assistance device according to claim 7, wherein the duration limiting means limit the maximum and minimum duration of the at least one period.

9. An implantable body function assistance device according to claim 8, wherein the at least one period is a period associated with sleep.

10. An implantable body function assistance device according to claim 9, wherein the cyclic physiologic needs are circadian physiologic needs associated with a wake/sleep cycle.

11. An implantable body function assistance device according to claim 1 or claim 2, wherein the model modifying means further comprise means for eliminating response to changes in physiologic needs not associated with a cyclic condition.

12. An implantable body function assistance device according to claim 11, wherein the response eliminating means comprise means for disregarding changes in physiologic needs for a predetermined duration after a selected event.

13. An implantable body function assistance device according to claim 12, wherein the selected event is the beginning of a waking period.

14. An implantable body function assistance device according to claim 13, wherein the cyclic physiologic needs are circadian physiologic needs associated with a wake/sleep cycle.

15. An implantable body function assistance device according to claim 1 or claim 2, wherein the parameter sensing means comprise means for sensing motion of the patient.

16. An implantable body function assistance device according to claim 15, wherein the motion sensing means comprise an accelerometer.

17. A method for assisting a body function having a generally cyclic real-time pattern of variable physiologic need, said method comprising the steps of:
producing a predictive model of cyclic real-time physiologic needs, the model comprising a plurality of periods, each period having a predicted duration and a predicted minimum physiologic need;
adjusting the rate of body function in real-time in accordance with the model of predicted cyclic physiologic needs;
sensing events correlated to actual physiologic need; and modifying the predictive model based on the sensed events.

18. A method according to claim 17, wherein the modifying step further comprises:
projecting a value of a parameter based on the sensed events;
comparing the projected value of the parameter to at least one prior value of the parameter in the model; and
adjusting the parameter based on the projected value and the prior value.

19. A method according to claim 18, wherein the adjusting step further comprises:
damping the rate of adjustment from the prior value of the parameter.

20. A method according to claim 18, wherein the step of sensing events comprises sensing motion of a patient.

21. A method according to claim 20, wherein the motion sensing step comprises sensing accelerations.

22. A method according to claim 19, wherein the damping step further comprises limiting the adjustment to not more than a predetermined value.

23. A method according to claim 22, wherein the comparing step comprises comparing the projected value of the parameter to an immediately preceding value of the parameter in the model.

24. A method according to claim 23, wherein the model producing step comprises:
producing a predictive model of circadian physiologic needs and
correlating the predictive model to a wake/sleep cycle.

25. A method according to claim 17, wherein the modifying step further comprises:
limiting the duration of at least one period of the predictive model.

26. A method according to claim 25, wherein the limiting step further comprises:
limiting the maximum duration of at least one selected period of the predictive model and
limiting the minimum duration of the selected at least one period.

27. A method according to claim 26, wherein the maximum duration limiting step is limiting the maximum duration of a period associated with sleep.

28. A method according to claim 26, wherein the minimum duration limiting step is limiting the minimum duration of a period associated with sleep.

29. A method according to claim 28, wherein the model producing step comprises:
producing a predictive model of circadian physiologic needs and
correlating the predictive model to a wake/sleep cycle.

30. A method according to claim 17, wherein the model modifying step further comprises:
eliminating responses to changes in physiologic needs not associated with a cyclic condition.

31. A method according to claim 30, wherein the eliminating step comprises:
disregarding changes in physiologic needs for a predetermined duration after a selected event.

32. A method according to claim 31, wherein the disregarding step comprises:
commencing a waking period and
disregarding changes in physiologic needs for a predetermined duration.

33. A method according to claim 31, wherein the model producing step comprises:
producing a predictive model of circadian physiologic needs and correlating the predictive model to a wake/sleep cycle.

* * * * *